US008463733B2

(12) United States Patent
Helfman et al.

(10) Patent No.: US 8,463,733 B2
(45) Date of Patent: Jun. 11, 2013

(54) USING DOTPLOTS FOR COMPARING AND FINDING PATTERNS IN SEQUENCES OF DATA POINTS

(75) Inventors: Jonathan Helfman, Half Moon Bay, CA (US); Joseph H. Goldberg, San Carlos, CA (US)

(73) Assignee: Oracle International Corporation, Redwood Shores, CA (US)

( * ) Notice: Subject to any disclaimer, the term of this patent is extended or adjusted under 35 U.S.C. 154(b) by 819 days.

(21) Appl. No.: 12/615,749

(22) Filed: Nov. 10, 2009

(65) Prior Publication Data

US 2010/0121812 A1  May 13, 2010

Related U.S. Application Data

(60) Provisional application No. 61/113,538, filed on Nov. 11, 2008.

(51) Int. Cl.
*G06F 17/00* (2006.01)
*G06N 7/04* (2006.01)
*G06F 19/22* (2006.01)

(52) U.S. Cl.
CPC ..................................... *G06F 19/22* (2013.01)
USPC .......................................................... 706/54

(58) Field of Classification Search
None
See application file for complete search history.

(56) References Cited

U.S. PATENT DOCUMENTS

| | | | |
|---|---|---|---|
| 4,859,050 A | 8/1989 | Borah et al. | |
| 4,973,149 A | 11/1990 | Hutchinson | |
| 5,517,021 A | 5/1996 | Kaufman et al. | |
| 5,649,061 A | 7/1997 | Smyth | |
| 5,726,916 A | 3/1998 | Smyth | |
| 6,381,339 B1 | 4/2002 | Brown et al. | |
| 6,755,527 B1 | 6/2004 | Goldberg | |
| 7,136,073 B2 | 11/2006 | Newman | |
| 7,339,580 B2 | 3/2008 | Westerman et al. | |
| 7,561,143 B1 | 7/2009 | Milekic | |
| 7,881,493 B1 | 2/2011 | Edwards et al. | |
| 7,922,670 B2 | 4/2011 | Jones et al. | |
| 2008/0222562 A1 | 9/2008 | Helfman et al. | |
| 2009/0043504 A1 | 2/2009 | Bandyopadhyay et al. | |
| 2010/0118030 A1 | 5/2010 | Helfman et al. | |
| 2010/0118032 A1 | 5/2010 | Helfman et al. | |

(Continued)

OTHER PUBLICATIONS

Gibbs, Adrian J. et al.; "The Diagram, a Method for Comparing Sequences"; 1970; Eur. J. BioChem. 16; pp. 1-11.*

(Continued)

*Primary Examiner* — Jeffrey A Gaffin
*Assistant Examiner* — Stanley K Hill
(74) *Attorney, Agent, or Firm* — Kilpatrick Townsend & Stockton LLP

(57) ABSTRACT

Embodiments of the invention provide systems and methods for analyzing sequential data. The sequential data can comprise a sequence of data points arranged in a particular order and thus representing a sequence. A number of such sequences can be analyzed, for example, to identify patterns or commonalities within the sequences or portions of sequences represented by the data. According to one embodiment, a method of identifying patterns in sequences of data points can comprise reading a set of sequential data. The sequential data can comprises a plurality of sequences and each of the plurality of sequences can represent an ordered sequence of tokens. A dotplot representing matches between each sequence of the plurality sequences can be generated. One or more patterns within the sequential data can then be identified based on the dotplot.

14 Claims, 9 Drawing Sheets

U.S. PATENT DOCUMENTS

2010/0118267 A1 5/2010 Helfman et al.
2010/0119111 A1 5/2010 Helfman et al.
2010/0119112 A1 5/2010 Helfman et al.

OTHER PUBLICATIONS

Sonnhammer, Erik L. L. et al.; "A dot-matrix program with dynamic threshold control suited for genomic DNA and protein sequence analysis"; 1995; Elsevier; Gene 167; pp. 1-10.*
Helfman, Jonathan; "Dotplot Patterns: A Literal Look at Pattern Languages"; 1996; ACM; Theory and Practice of Object Systems—Special issue on patterns, vol. 2, Issue 1; pp. 31-41.*
Jareborg, Niclas et al.; "Alfresco—A Workbench for Comparative Genomic Sequence Analysis"; 2000; Genome Res. 2000; pp. 1148-1157.*
Jensen, Kyle L. et al.; "A generic motif discovery algorithm for sequential data"; 2006; Oxford University Press; Bioinformatics, vol. 22, No. 1; pp. 21-28.*
Arun, K. S. et al.; "Least-Squares Fitting of Two 3-D Point Sets"; 1987; IEEE; Transactions on Pattern Analysis and Machine Intelligence, vol. PAMI-9, No. 5; pp. 698-700.*
Tobii Eye Tracking, "Tobii Eye Tracking: Research with Vision," 8 pages downloaded on Dec. 28, 2009 at URL: www.tobii.com.
Tobii Studio 2 brochure, "Comprehensive Eye Tracking analysis & visualization software," 5 pages downloaded on Dec. 28, 2009 at URL: www.tobii.com.
Tobii® Technology, "Tobii StudioTM Tobii Technology," Product Description, Revision 2.0, May 2009, pp. 1-26 downloaded on Dec. 28, 2009 at URL: www.tobii.com.
Tobii® Technology, "Tobii T/X series Eye Trackers," Product Description, Revision 2.0, May 2009, pp. 1-22 downloaded on Dec. 28, 2009 at URL: www.tobii.com.
U.S. Appl. No. 12/615,736, filed Nov. 10, 2009, Helfman et al.
U.S. Appl. No. 12/615,763, filed Nov. 10, 2009, Helfman et al.
U.S. Appl. No. 12/616,016, filed Nov. 10, 2009, Helfman et al.
U.S. Appl. No. 12/616,030, filed Nov. 10, 2009, Helfman et al.
U.S. Appl. No. 12/615,035, filed Nov. 10, 2009, Helfman et al.
Tobii T60 & T120 Eye Trackers, "Plug & Play Eye Trackers for On-Screen Research," 2 pages downloaded on Dec. 28, 2009 at URL: www.tobii.com.
Tobii T60 XL Eye Tracker, "Widescreen Eye Tracker for large stimulus display," 2 pages downloaded on Dec. 28, 2009 at URL: www.tobii.com.
Tobii X60 & X120 Eye Tracker, "Flexible Eye Trackers for Studies of Physical Objects," 2 pages downloaded on Dec. 28, 2009 at URL: www.tobii.com.
Aula, A., et al., "Multilingual Search Strategies," in Proceedings of CHI 2009—Spotlight on Works in Progress—Session 1, Boston, MA, USA, Apr. 4-9, 2009, pp. 3865-3870, ACM Press, Copyright 2009.
Beymer, D., et al., "WebGazeAnalyzer: A System for Capturing and Analyzing Web Reading Behavior Using Eye Gaze," in Proceedings of CHI 2005, Portland, Oregon, USA, Apr. 2-7, 2005, pp. 1913-1916, ACM Press, Copyright 2005.
Bednarik, R., et al., "Temporal Eye-Tracking Data: Evolution of Debugging Strategies with Multiple Representations," in proceedings of 2008 Symposium on Eye Tracking Research & Applications, Savannah, Georgia, Mar. 26-28, 2008, pp. 99-102, ACM Press, Copyright 2008.
Bojko, A., "Informative or Misleading? Heatmaps Deconstructed," J.A. Jacko (Ed.): Human-Computer Interaction, Part I, HCII 2009, LNCS 5610, 2009, pp. 30-39, Springer-Verlag Berlin Heidelberg.
Bojko, A., "Using Eye Tracking to Compare Web Page Designs: A Case Study," Journal of Usability Studies, May 2006, pp. 112-120, Issue 3, vol. 1.
Church, K., et al., "Dotplot: a Program for Exploring Self-Similarity in Millions of Lines of Text and Code," The Journal of Computational and Graphical Statistics, 1993, 12 pages (pp. 153-174 in publication), vol. 2, No. 2.
Cinar, M., "Eye Tracking Method to Compare the Usability of University Web Sites: A Case Study," M. Kurosu (Ed.): Human Centered Design, HCII 2009, LNCS 5619, 2009, pp. 671-678, Springer-Verlag Berlin Heidelberg.
Cutrell, E., et al., "What Are You Looking For? An Eye-tracking Study of Information Usage in Web Search," in Proceedings of CHI 2007, San Jose, California, USA, Apr. 28-May 3, 2007, 10 pages (pp. 407-416 in publication), ACM, Copyright 2007.
"Eyetools Eyetracking Research: But what does it all mean? Understanding eye-tracking results (Part 4)," Sep. 6, 2007, pp. 1-3, downloaded on Mar. 19, 2009 at URL: http://blog.eyetools.net/eyetools_research/2007/09/but-what-does-2.html.
Feusner, M., et al., "Testing for Statistically Significant Differences Between Groups of Scan Patterns," in Proceedings of 2008 Symposium on Eye Tracking Research & Applications, Savannah, Georgia, Mar. 26-28, 2008, pp. 43-46, ACM Press, Copyright 2008.
Goldberg, J. H., et al., "Computer Interface Evaluation Using Eye Movements: Methods and Constructs," International Journal of Industrial Ergonomics, 1999, pp. 631-645, vol. 24.
Goldberg, J. H., et al., "Eye Movement-Based Evaluation of the Computer Interface," Advances in Occupational Ergonomics and Safety, S. Kumar, (Ed.), 1998, pp. 529-532, IOS Press.
Goldberg, J. H., et al., "Eye Tracking in Web Search Tasks: Design Implications," in Proceedings of 2002 Symposium on Eye Tracking Research & Applications, ACM Press, 2002, 8 pages.
Granka, L., et al., "Incorporating Eyetracking into User Studies at Google," Workshop paper presented at CHI 2006, 2006, 2 pages, ACM Press.
Granka, L., et al., "Location Location Location: Viewing Patterns on WWW Pages," in Proceedings of the 2006 Symposium on Eye Tracking Research & Applications, San Diego, California, Mar. 27-29, 2006, p. 43, ACM Press, Copyright 2006.
Guan, Z., et al., "An Eye Tracking Study of the Effect of Target Rank on Web Search," in Proceedings of CHI 2007, San Jose, California, USA, Apr. 28-May 3, 2007, 4 pages (pp. 417-420 in publication), ACM Press, Copyright 2007.
Habuchi, Y., et al., "Comparison of Eye Movements in Searching for Easy-to-Find and Hard-to-Find Information in a Hierarchically Organized Information Structure," in Proceedings of the 2008 Symposium on Eye Tracking Research & Applications, Savannah, Georgia, Mar. 26-28, 2008, pp. 131-134, ACM Press, Copyright 2008.
Harris, R. L., "Information Graphics: A Comprehensive Illustrated Reference," 1999, pp. 164-177 and p. 191, Management Graphics, Atlanta, GA, Oxford University Press, New York, Copyright 1999.
Helfman, J. I., "Dotplot Patterns: A Literal Look at Pattern Languages," TAPOS, 2(1):31-41, 1995.
Helfman, J. I., "Similarity Patterns in Language," Proceedings of the IEEE Symposium on Visual Language, 1994, 3 pages (pp. 173-175 in publication), IEEE Press.
Hembrooke, H., et al., "Averaging Scan Patterns and What They Can Tell Us," in Proceedings of the 2006 symposium on Eye Tracking Research & Applications, San Diego, California, Mar. 27-29, 2006, p. 41, ACM Press, Copyright 2006.
Heminghous, J., et al., "iComp: A Tool for Scanpath Visualization and Comparison," in Proceedings of the 2006 Applied Perception in Graphics and Visualization, Boston, Massachusetts, Jul. 28-29, 2006, p. 152, ACM Press, Copyright 2006.
Hornof, A. J., "Cognitive Strategies and Eye Movements for Searching Hierarchical Computer Displays," Paper: Modeling User Behavior, in Proceedings of CHI 2003, Ft. Lauderdale, Florida, USA, Apr. 5-10, 2003, pp. 249-256, CHI 2003: New Horizons, Vol. No. 5, Issue No. 1, ACM Press, Copyright 2003.
Huang, Y., et al., "Rapid and Sensitive Dot-matrix Methods for Genome Analysis," Bioinformatics Advance Access, Jan. 22, 2004, pp. 460-466, vol. 20, No. 4, Oxford University Press, Copyright 2004, downloaded on Mar. 15, 2010 from URL : http://bioinformatics.oxfordjournals.org.
Josephson, S., et al., "Visual Attention to Repeated Internet Images: Testing the Scanpath Theory on the World Wide Web," in Proceedings of the 2002 Symposium on Eye Tracking Research & Applications, New Orleans, Louisiana, USA, pp. 43-49, ACM Press, Copyright 2002.

Levenshtein, V. I., "Binary Codes Capable of Correcting Deletions, Insertions, and Reversals," Cybernetics and Control Theory, Doklady Physics, Feb. 1966, pp. 707-710, vol. 10, No. 8.

Lorigo, L., et al., "Eye Tracking and Online Search: Lessons Learned and Challenges Ahead," Journal of the American Society for Information Science and Technology, 2008, pp. 1041-1052, vol. 59, No. 7, Copyright 2008.

Mankowski, W. C., et al., "Finding Canonical Behaviors in User Protocols," in Proceedings of CHI 2009, Boston, MA, USA, Apr. 4-9, 2009, 4 pages, ACM Press, Copyright 2009.

Marshall, S. P., "Identifying Cognitive State from Eye Metrics," Aviation, Space, and Environmental Medicine, May 2007, pp. B165-B186, vol. 78, No. 5, Section II.

Matsuda, Y., et al., "An Analysis of Eye Movements During Browsing Multiple Search Results Pages," J.A. Jacko (Ed.): Human-Computer Interaction, Part I, HCII, LNCS 5610, pp. 121-130, Copyright 2009 Springer-Verlag Berlin Heidelberg, Copyright 2009.

Myers, C. W., "Toward a Method of Objectively Determining Scanpath Similarity," [Abstract], Journal of Vision, Sep. 23, 2005, 2 pages, vol. 5, No. 8, Abstract 693, downloaded on Jan. 5, 2010 from URL: http://www.journalofvision.org/5/8/693/.

Najemnik, J., et al., "Optimal Eye Movement Strategies in Visual Search," Nature, Mar. 17, 2005, pp. 387-391, vol. 434, Copyright 2005 Nature Publishing Group.

Raiha, K., et al., "Static Visualization of Temporal Eye-Tracking Data," M.F. Costabile and F. Paterno (Eds.): INTERACT 2005, LNCS 3585, 2005, pp. 946-949, Copyright IFIP International Federation for Information Processing 2005.

Rantala, H., "Eye2i: Coordinated Multiple Views for Gaze Data," in Proceedings of the 2008 Symposium on Eye Tracking Research & Applications, Savannah, Georgia, Mar. 26-28, 2008, pp. 147-148, ACM Press, Copyright 2008.

Salvucci, D. D., et al., "Identifying Fixations and Saccades in Eye-Tracking Protocols," in Proceedings of the 2000 Symposium on Eye Tracking Research & Applications, Palm Beach Gardens, FL, USA, pp. 71-78, ACM Press, Copyright 2000.

Santella, A., et al., "Robust Clustering of Eye Movement Recordings for Quantification of Visual Interest," in Proceedings of the 2004 Symposium on Eye Tracking Research & Applications, San Antonio, Texas, 2004, pp. 27-34, ACM Press, Copyright 2004.

Smith, T. F., et al., "Identification of Common Molecular Subsequences," Reprinted from Journal of Molecular Biology, 1981, pp. 195-197, vol. 147, Academic Press, Copyright 1980.

Tufte, E. R., "Beautiful Evidence," Sparklines: Intense Word-Sized Graphics, Graphic Press LLC, Cheshire, CT., pp. 46-63, Copyright 2006.

Tufte, E. R., "The Visual Display of Quantitative Information," Theory of Data Graphics, Graphics Press LLC, Cheshire, CT., pp. 170-175, Copyright 1983.

Uwano, H., et al., "Analyzing Individual Performance of Source Code Review Using Reviewers' Eye Movement," in Proceedings of 2006 Eye Tracking Research & Applications, San Diego, California, Mar. 27-29, pp. 133-140, ACM Press.

Wattenberg, M., "Arc Diagrams: Visualizing Structure in Strings," in Proceedings of the IEEE Symposium on Information Visualization (InfoVis'02), 2002, 8 pages, IEEE Computer Society.

Werman, M., et al., "A Bayesian Method for Fitting Parametric and Nonparametric Models to Noisy Data," IEEE Transactions on Pattern Analysis and Machine Intelligence, May 2001, pp. 528-534, vol. 23, No. 5, Copyright 2001.

West, J. M., et al., "EyePatterns: Software for Identifying Patterns and Similarities Across Fixation Sequences," in Proceedings of the 2006 Symposium on Eye Tracking Research & Applications, San Diego, California, Mar. 27-29, 2006, pp. 149-154, ACM Press, Copyright 2006.

Wooding, D. S., "Eye Movements of Large Populations: II. Deriving Regions of Interest, Coverage, and Similarity Using Fixation Maps," Behavior Research Methods, Instruments, & Computers, 2002, pp. 518-528, vol. 34, No. 4, Psychonomic Society, Inc., Copyright 2002.

Aula, A., et al., "Eye-tracking Reveals the Personal Styles for Search Result Evaluation," in Proceedings of Human-Computer Interaction, Tampere Unit for Computer-Human Interaction (TAUCHI), 2005, pp. 135-138, [Can also be found in Proceedings of INTERACT 2005, Int. Fed. Info Proc., pp. 1058-1061.]

Goldberg, J. H., et al., "Scanpath Clustering and Aggregation," Applications User Experience, Oracle USA, 8 pages, Proceedings of the Mar. 2010 Eye Tracking Research and Applications, ACM Press.

Goldberg, J. H., et al., "Visual Scanpath Representation," Applications User Experience, Oracle USA, 8 pages, Proceedings of the Mar. 2010 Eye Tracking Research and Applications, ACM Press.

Duchowski, A., "Eye-Based Interaction in Graphical Systems: Theory & Practice," Siggraph 2000, 25 pages.

Torstling, A., "The Mean Gaze Path: Information Reduction and Non-Intrusive Attention Detection for Eye Tracking," Masters Degree Project, KTH Royal Institute of Technology, Stockholm, Sweden, Oct. 17, 2007, 64 pages.

U.S. Appl. No. 12/615,736, filed Nov. 10, 2009, Office Action mailed May 24, 2012, 4 pages.

U.S. Appl. No. 12/616,030, filed Nov. 10, 2009, Office Action mailed Jul. 20, 2012, 11 pages.

U.S. Appl. No. 12/616,035, filed Nov. 10, 2009, Office Action mailed Jul. 23, 2012, 10 pages.

Franklin, K. M., et al., "A Path Based Model for Sonification," Proceedings of the Eighth International Conference on Information Visualisation, Jul. 2004, 6 pages.

U.S. Appl. No. 12/615,763, filed Nov. 10, 2009, Office Action mailed Sep. 10, 2012, 13 pages.

U.S. Appl. No. 12/616,016, filed Nov. 10, 2009, Office Action mailed Jun. 20, 2012, 9 pages.

* cited by examiner

USING DOTPLOTS FOR COMPARING AND FINDING PATTERNS IN SEQUENCES OF DATA POINTS

CROSS-REFERENCES TO RELATED APPLICATIONS

The present application claims benefit under 35 USC 119 (e) of U.S. Provisional Application No. 61/113,538, filed on Nov. 11, 2008, entitled "Techniques For Analyzing Paths," the entire contents of which are incorporated herein by reference for all purposes. The present application is also related to U.S. patent application Ser. No. 12/615,763, filed Nov. 10, 2009, entitled "Time Expansion for Displaying Path Information", which is filed concurrently herewith and incorporated herein by reference for all purposes.

BACKGROUND

Embodiments of the present invention relate to analyzing sequential data, and more specifically to finding patterns within a dataset representing a number of sequences or paths.

Analysis of paths is performed in various different fields or domains. For example, in eye tracking analysis, scanpaths representing users' eye movements while viewing a scene may be analyzed to determine high-level scanning strategies. The scanning strategies determined from such an analysis may be used to improve product designs. For example, by studying scanpaths for users viewing a web page, common viewing trends may be determined and used to improve the web page layout. Various other types of analyses on paths may be performed in other fields. Accordingly, new and improved techniques are always desirable for analyzing and displaying path-related information that can provide insight into characteristics of the path and that facilitate comparisons of paths.

BRIEF SUMMARY

Embodiments of the invention provide systems and methods for analyzing sequential data. The sequential data can comprise a sequence of data points arranged in a particular order. A number of such sequences can be analyzed, for example, to identify patterns or commonalities within the sequences or portions of sequences represented by the data. According to one embodiment, a method of identifying patterns in sequences of data points can comprise reading a set of sequential data. The sequential data can comprise a plurality of sequences and each of the plurality of sequences can consist of an ordered sequence of tokens. A dotplot representing matches between each path of the plurality sequences can be generated. One or more patterns within the sequential data can then be identified based on the dotplot.

Identifying one or more patterns can comprise determining a dotplot sub-matrix comprising token matches between two sequences. Points in the sub-matrix can correspond to matching tokens in the corresponding sub-sequences. The points can be filtered against a pre-determined high-pass threshold and a linear regression line can be fitted to the filtered points. A determination can be made as to whether statistical evidence for a line exists within the filtered points based on attempting to fit a linear regression line to the filtered points. If evidence for a line exists, variance criterion can be computed based on Euclidean distances between the regression line and the filtered points. The filtered points can be further filtered to those within the variance criterion and the linear regression line can be recomputed using the points within the variance criterion. Linear relationships between the points can be identified based on the recomputed linear regression line and removed from the set of points. In some cases, identifying one or more patterns can further comprise identifying another linear relationship within the dataset by repeating said fitting a linear regression line to the filtered points, determining whether evidence for a line exists within the filtered points based on said fitting a linear regression line to the filtered points, computing variance criterion based on Euclidean distances between the regression line and the filtered points, filtering the filtered points to those within the variance criterion, re-computing the linear regression line using the points within the variance criterion, identifying linear relationships between the points within the variance criterion based on the recomputed linear regression line, and removing the points identified as having linear relationships from the set of points.

The tokens of the sequential data can represent, for example, data points comprising fixation points of eye tracking data and the sequences can represent scanpaths. In another example, the tokens can represent data points comprising Uniform Resource Locators (URLs) and the sequences can represent sequences of requested URLs in a client web browsing session. In other cases, the tokens can represent data points comprising Uniform Resource Locators (URLs) and the sequences can represent sequences of requested URLs in a web server log file. In yet another example, the tokens can represent data points comprising text strings and the sequences can represent sequences of the strings within one or more documents. In still another example, the tokens can represent data points comprising stock prices and the sequences can represent the stock prices over time. In another case, the tokens can represent genes and the sequences can represent sequences of DeoxyriboNucleic Acid (DNA) or RiboNucleic Acid (RNA).

According to another embodiment, a system for identifying one or more patterns in a plurality of sequences can comprise a processor and a memory communicatively coupled with and readable by the processor. The memory can have stored therein a series of instructions which, when executed by the processor, cause the processor to read a set of sequential data. The sequential data can comprise a plurality of sequences, each of the plurality of sequences consisting of ordered sequence of tokens. A dotplot can be generated based on the tokens and can represent matches between each sequence of the plurality sequences. One or more patterns within the sequential data can be identified based on the dotplot.

The instructions can further cause the processor to identify one or more patterns within the sequential data based on the dotplot by determining a dotplot sub-matrix comprising token matches between two sequences. Points in the sub-matrix can correspond to matching tokens in the corresponding sub-sequences. The points can be filtered against a pre-determined high-pass threshold and a linear regression line can be fitted to the filtered points. A determination can be made as to whether statistical evidence for a line exists within the filtered points based on attempting to fit a linear regression line to the filtered points. If evidence for a line exists, variance criterion can be computed based on Euclidean distances between the regression line and the filtered points. The filtered points can be further filtered to those within the variance criterion and the linear regression line can be recomputed using the points within the variance criterion. Linear relationships between the points can be identified based on the recomputed linear regression line and removed from the set of points. In some cases, identifying one or more patterns can further comprise identifying another linear relationship within the dataset by repeating said fitting a linear regression line to the filtered points, determining whether evidence for a line exists within the filtered points based on said fitting a linear regression line to the filtered points, computing variance criterion based on Euclidean distances between the regression line and the filtered points, filtering the filtered points to those within the variance criterion, re-computing the linear regression line using the points within the variance criterion, identifying linear relationships between the points within the variance criterion based on the recomputed linear regression line, and removing the points identified as having linear relationships from the set of points.

According to yet another embodiment, a machine-readable medium can have stored thereon a series of instructions which, when executed by a processor, cause the processor to identify one or more patterns in a plurality of sequences by reading a set of sequential data with a sequence analysis system. The sequential data can comprise a plurality of sequences, each of the plurality of sequences consisting of an ordered sequence of tokens. A dotplot can be generated based on the tokens and can represent matches between each sequence of the plurality sequences. One or more patterns within the sequential data can be identified based on the dotplot.

Identifying one or more patterns can comprise determining a dotplot sub-matrix comprising token matches between two sequences. Points in the sub-matrix can correspond to matching tokens in the corresponding sub-sequences. The points can be filtered against a pre-determined high-pass threshold and a linear regression line can be fitted to the filtered points. A determination can be made as to whether statistical evidence for a line exists within the filtered points based on attempting to fit a linear regression line to the filtered points. If evidence for a line exists, variance criterion can be computed based on Euclidean distances between the regression line and the filtered points. The filtered points can be further filtered to those within the variance criterion and the linear regression line can be recomputed using the points within the variance criterion. Linear relationships between the points can be identified based on the recomputed linear regression line and removed from the set of points. In some cases, identifying one or more patterns can further comprise identifying another linear relationship within the dataset by repeating said fitting a linear regression line to the filtered points, determining whether evidence for a line exists within the filtered points based on said fitting a linear regression line to the filtered points, computing variance criterion based on Euclidean distances between the regression line and the filtered points, filtering the filtered points to those within the variance criterion, re-computing the linear regression line using the points within the variance criterion, identifying linear relationships between the points within the variance criterion based on the recomputed linear regression line, and removing the points identified as having linear relationships from the set of points.

DETAILED DESCRIPTION

Figure 1:
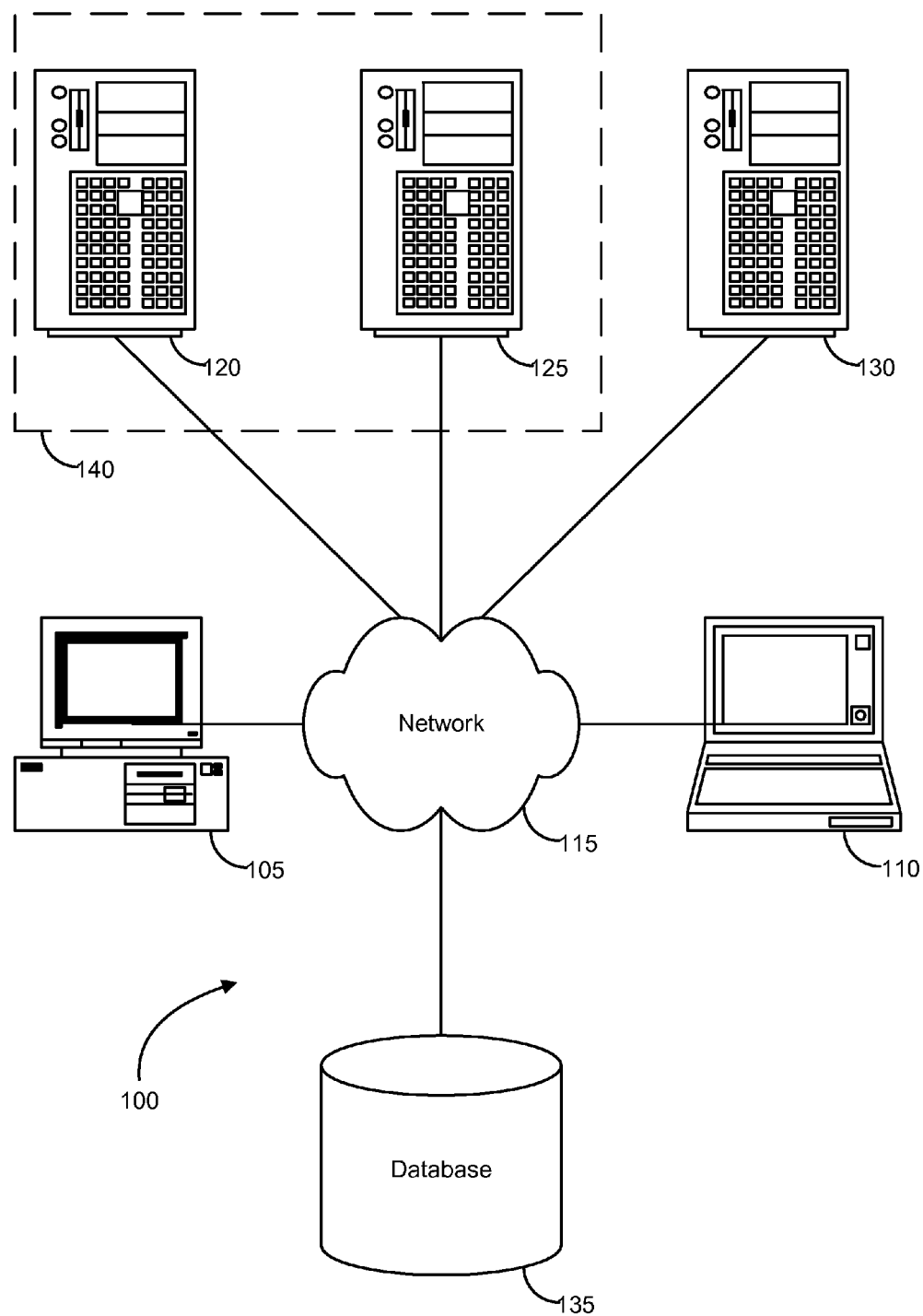
FIG. 1 is a block diagram illustrating components of an exemplary operating environment in which various embodiments of the present invention may be implemented.

In the following description, for the purposes of explanation, numerous specific details are set forth in order to provide a thorough understanding of various embodiments of the present invention. It will be apparent, however, to one skilled in the art that embodiments of the present invention may be practiced without some of these specific details. In other instances, well-known structures and devices are shown in block diagram form.

The ensuing description provides exemplary embodiments only, and is not intended to limit the scope, applicability, or configuration of the disclosure. Rather, the ensuing description of the exemplary embodiments will provide those skilled in the art with an enabling description for implementing an exemplary embodiment. It should be understood that various changes may be made in the function and arrangement of elements without departing from the spirit and scope of the invention as set forth in the appended claims.

Specific details are given in the following description to provide a thorough understanding of the embodiments. However, it will be understood by one of ordinary skill in the art that the embodiments may be practiced without these specific details. For example, circuits, systems, networks, processes, and other components may be shown as components in block diagram form in order not to obscure the embodiments in unnecessary detail. In other instances, well-known circuits, processes, algorithms, structures, and techniques may be shown without unnecessary detail in order to avoid obscuring the embodiments.

Also, it is noted that individual embodiments may be described as a process, which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in a figure. A process may correspond to a method, a function, a procedure, a subroutine, a subprogram, etc. When a process corresponds to a function, its termination can correspond to a return of the function to the calling function or the main function.

The term "machine-readable medium" includes, but is not limited to portable or fixed storage devices, optical storage devices, wireless channels and various other mediums capable of storing, containing or carrying instruction(s) and/or data. A code segment or machine-executable instructions may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium. A processor(s) may perform the necessary tasks.

Embodiments of the present invention provide systems and methods for analyzing sequential data, for example, to identify patterns or commonalities within paths or portions of paths represented by the data. As the term is used herein, a path may be defined as a sequence of two or more points. The first point in the sequence of points may be referred to as the start point of the path and the last point in the sequence may be referred to as the end point of the path. The portion of a path between any two consecutive points in the sequence of points may be referred to as a path segment. A path may comprise one or more segments.

A sequence may be any list of tokens or symbols in a particular order. Examples of sequences can include but are not limited to words in a query, words in a document, symbols in a computer program's source code, scanpaths, i.e., sequences of eye tracking fixation points as determined by an eye tracking system, sequences of requested URLs in a user's web browsing session, sequences of requested URLs in a web server's log file, etc.

Thus, there are different types of paths considered to be within the scope of the term as used herein. Examples described below have been described with reference to a specific type of path, referred to as a scanpath, which is used to track eye movements. A scanpath is a path that an eye follows when viewing a scene. A scanpath is defined by a sequence of fixation points (or gaze locations). A path segment between two consecutive fixation points in the sequence of fixation points is referred to as a saccade. A scanpath is thus a sequence of fixation points connected by saccades during scene viewing where the saccades represent eye movements between fixation points. For purposes of simplicity, the scanpaths described below are 1- or 2-dimensional paths. The teachings of the present invention may however also be applied to paths in multiple dimensions.

However, it should be understood that, while embodiments of the present invention have been described in context of scanpaths, this is not intended to limit the scope of the present invention as recited in the claims to scanpaths. Teachings of the present invention may also be applied to other types of paths or sequences occurring in various different domains such as a stock price graph, a path followed by a car between a start and an end destination, and the like. Various additional details of embodiments of the present invention will be described below with reference to the figures.

FIG. 1 is a block diagram illustrating components of an exemplary operating environment in which various embodiments of the present invention may be implemented. The system 100 can include one or more user computers 105, 110, which may be used to operate a client, whether a dedicate application, web browser, etc. The user computers 105, 110 can be general purpose personal computers (including, merely by way of example, personal computers and/or laptop computers running various versions of Microsoft Corp.'s Windows and/or Apple Corp.'s Macintosh operating systems) and/or workstation computers running any of a variety of commercially-available UNIX or UNIX-like operating systems (including without limitation, the variety of GNU/Linux operating systems). These user computers 105, 110 may also have any of a variety of applications, including one or more development systems, database client and/or server applications, and web browser applications. Alternatively, the user computers 105, 110 may be any other electronic device, such as a thin-client computer, Internet-enabled mobile telephone, and/or personal digital assistant, capable of communicating via a network (e.g., the network 115 described below) and/or displaying and navigating web pages or other types of electronic documents. Although the exemplary system 100 is shown with two user computers, any number of user computers may be supported.

In some embodiments, the system 100 may also include a network 115. The network may can be any type of network familiar to those skilled in the art that can support data communications using any of a variety of commercially-available protocols, including without limitation TCP/IP, SNA, IPX, AppleTalk, and the like. Merely by way of example, the network 115 maybe a local area network ("LAN"), such as an Ethernet network, a Token-Ring network and/or the like; a wide-area network; a virtual network, including without limitation a virtual private network ("VPN"); the Internet; an intranet; an extranet; a public switched telephone network ("PSTN"); an infra-red network; a wireless network (e.g., a network operating under any of the IEEE 802.11 suite of protocols, the Bluetooth protocol known in the art, and/or any other wireless protocol); and/or any combination of these and/or other networks such as GSM, GPRS, EDGE, UMTS, 3G, 2.5 G, CDMA, CDMA2000, WCDMA, EVDO etc.

The system may also include one or more server computers 120, 125, 130 which can be general purpose computers and/or specialized server computers (including, merely by way of example, PC servers, UNIX servers, mid-range servers, mainframe computers rack-mounted servers, etc.). One or more of the servers (e.g., 130) may be dedicated to running applications, such as a business application, a web server, application server, etc. Such servers may be used to process requests from user computers 105, 110. The applications can also include any number of applications for controlling access to resources of the servers 120, 125, 130.

The web server can be running an operating system including any of those discussed above, as well as any commercially-available server operating systems. The web server can also run any of a variety of server applications and/or mid-tier applications, including HTTP servers, FTP servers, CGI servers, database servers, Java servers, business applications, and the like. The server(s) also may be one or more computers which can be capable of executing programs or scripts in response to the user computers 105, 110. As one example, a server may execute one or more web applications. The web application may be implemented as one or more scripts or programs written in any programming language, such as Java™, C, C# or C++, and/or any scripting language, such as Perl, Python, or TCL, as well as combinations of any programming/scripting languages. The server(s) may also include database servers, including without limitation those commercially available from Oracle®, Microsoft®, Sybase®, IBM® and the like, which can process requests from database clients running on a user computer 105, 110.

In some embodiments, an application server may create web pages dynamically for displaying on an end-user (client) system. The web pages created by the web application server may be forwarded to a user computer 105 via a web server. Similarly, the web server can receive web page requests and/or input data from a user computer and can forward the web page requests and/or input data to an application and/or a database server. Those skilled in the art will recognize that the functions described with respect to various types of servers may be performed by a single server and/or a plurality of specialized servers, depending on implementation-specific needs and parameters.

The system 100 may also include one or more databases 135. The database(s) 135 may reside in a variety of locations. By way of example, a database 135 may reside on a storage medium local to (and/or resident in) one or more of the computers 105, 110, 115, 125, 130. Alternatively, it may be remote from any or all of the computers 105, 110, 115, 125, 130, and/or in communication (e.g., via the network 120) with one or more of these. In a particular set of embodiments, the database 135 may reside in a storage-area network ("SAN") familiar to those skilled in the art. Similarly, any necessary files for performing the functions attributed to the computers 105, 110, 115, 125, 130 may be stored locally on the respective computer and/or remotely, as appropriate. In one set of embodiments, the database 135 may be a relational database, such as Oracle 10 g, that is adapted to store, update, and retrieve data in response to SQL-formatted commands.

Figure 2:
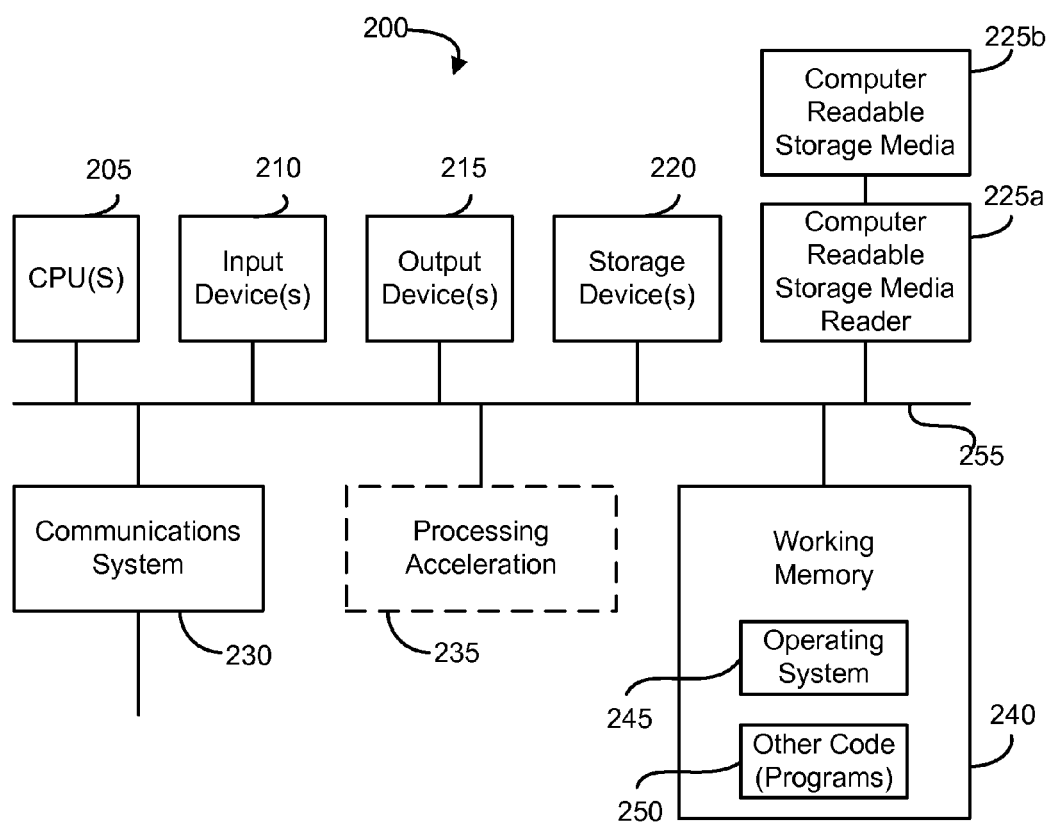
FIG. 2 is a block diagram illustrating an exemplary computer system in which embodiments of the present invention may be implemented.

FIG. 2 illustrates an exemplary computer system 200, in which various embodiments of the present invention may be implemented. The system 200 may be used to implement any of the computer systems described above. The computer system 200 is shown comprising hardware elements that may be electrically coupled via a bus 255. The hardware elements may include one or more central processing units (CPUs) 205, one or more input devices 210 (e.g., a mouse, a keyboard, etc.), and one or more output devices 215 (e.g., a display device, a printer, etc.). The computer system 200 may also include one or more storage device 220. By way of example, storage device(s) 220 may be disk drives, optical storage devices, solid-state storage device such as a random access memory ("RAM") and/or a read-only memory ("ROM"), which can be programmable, flash-updateable and/or the like.

The computer system 200 may additionally include a computer-readable storage media reader 225a, a communications system 230 (e.g., a modem, a network card (wireless or wired), an infra-red communication device, etc.), and working memory 240, which may include RAM and ROM devices as described above. In some embodiments, the computer system 200 may also include a processing acceleration unit 235, which can include a DSP, a special-purpose processor and/or the like.

The computer-readable storage media reader 225a can further be connected to a computer-readable storage medium 225b, together (and, optionally, in combination with storage device(s) 220) comprehensively representing remote, local, fixed, and/or removable storage devices plus storage media for temporarily and/or more permanently containing computer-readable information. The communications system 230 may permit data to be exchanged with the network 220 and/or any other computer described above with respect to the system 200.

The computer system 200 may also comprise software elements, shown as being currently located within a working memory 240, including an operating system 245 and/or other code 250, such as an application program (which may be a client application, web browser, mid-tier application, RDBMS, etc.). It should be appreciated that alternate embodiments of a computer system 200 may have numerous variations from that described above. For example, customized hardware might also be used and/or particular elements might be implemented in hardware, software (including portable software, such as applets), or both. Further, connection to other computing devices such as network input/output devices may be employed. Software of computer system 200 may include code 250 for implementing embodiments of the present invention as described herein.

As noted above, embodiments of the present invention provide for analyzing sequential data including but not limited to paths such as eye tracking data including scanpaths representing users' eye movements while viewing a stimulus image or other scene. The eye tracking data can represent a number of different scanpaths and can be analyzed, for example, to find patterns or commonality between the scanpaths. According to one embodiment, analyzing eye tracking data with a path analysis system such as the computer system 200 described above can comprise receiving the eye tracking data at the path analysis system. The eye tracking data, which can be obtained by the system in a number of different ways as will be described below, can include a plurality of scanpaths, each scanpath representing a sequence of regions of interest on a scene such as a stimulus image displayed by the system. A dotplot can be generated by the system that represents matches between each of the plurality of scanpaths. One or more patterns within the eye tracking data can then be identified by the system based on the dotplot.

Figure 3:
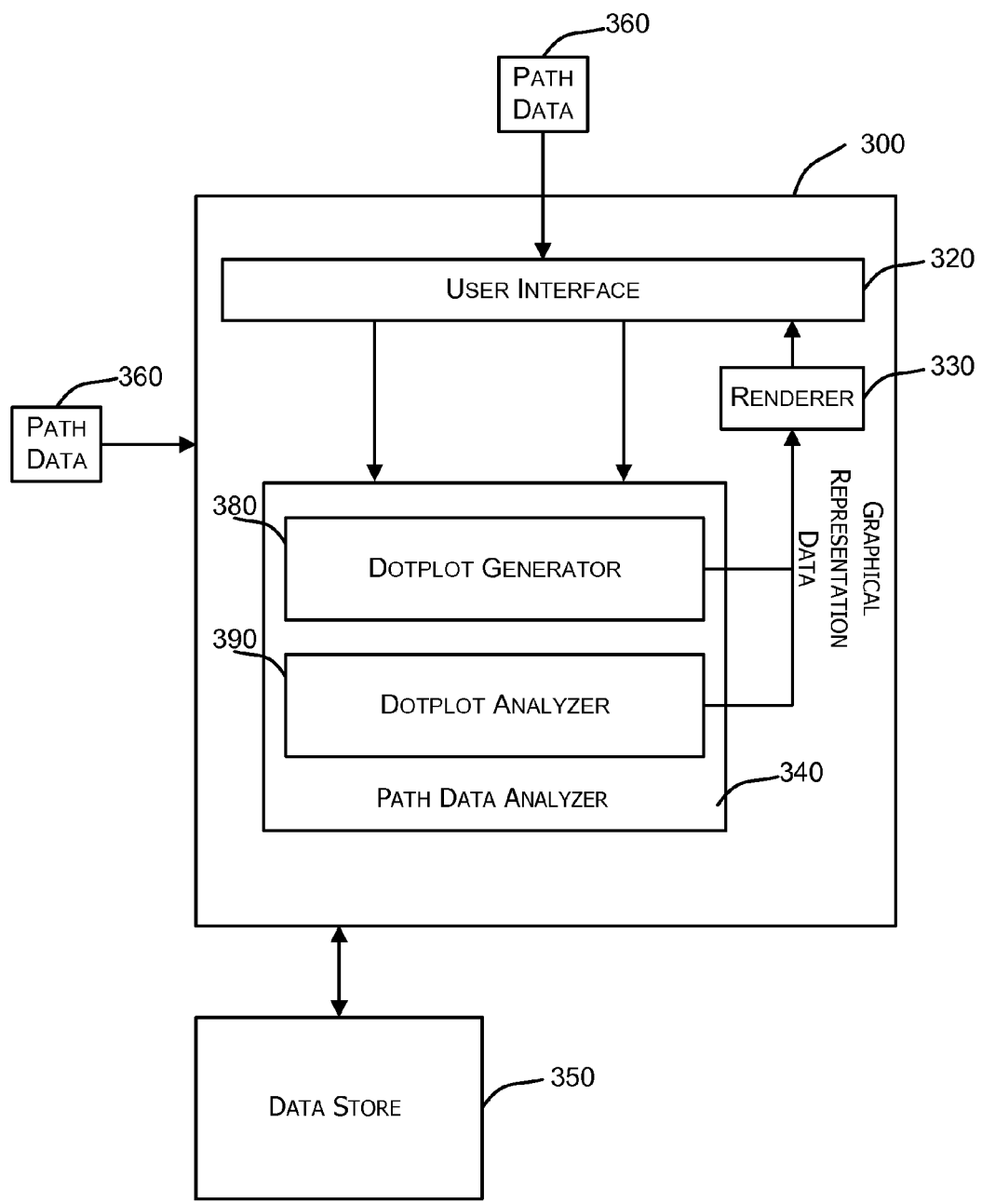
FIG. 3 is a block diagram illustrating, at a high-level, functional components of a system for analyzing eye tracking data according to one embodiment of the present invention.

FIG. 3 is a block diagram illustrating, at a high-level, functional components of a system for analyzing eye tracking data according to one embodiment of the present invention. In this example, the path analysis system 300 comprises several components including a user interface 320, a renderer 330, and a path data analyzer 340. The various components may be implemented in hardware, or software (e.g., code, instructions, program executed by a processor), or combinations thereof. Path analysis system 300 may be coupled to a data store 350 that is configured to store data related to processing performed by system 300. For example, path data (e.g., scanpath data) may be stored in data store 350.

User interface 320 provides an interface for receiving information from a user of path analysis system 300 and for outputting information from path analysis system 300. For example, a user of path analysis system 300 may enter path data 360 for a path to be analyzed via user interface 320. Additionally or alternatively, a user of path analysis system 300 may enter commands or instructions via user interface 320 to cause path analysis system 300 to obtain or receive path data 360 from another source. It should be noted, however, that a user interface is entirely optional to the present invention, which does not rely on the existence of a user interface in any way.

System 300 may additionally or alternatively receive path data 360 from various other sources. In one embodiment, the path data may be received from sources such as from an eye tracker device. For example, information regarding the fixation points and saccadic eye movements between the fixation points, i.e., path data 360, may be gathered using eye tracking devices such as devices provided by Tobii (e.g., Tobii T60 eye tracker). An eye-tracking device such as the Tobii T60 eye tracker is capable of capturing information related to the saccadic eye activity including location of fixation points, fixation durations, and other data related to a scene or stimulus image, such as a webpage for example, while the user views the scene. Such an exemplary user interface is described in greater detail below with reference to FIG. 4 The Tobii T60 uses infrared light sources and cameras to gather information about the user's eye movements while viewing a scene.

The path data may be received in various formats, for example, depending upon the source of the data. In one embodiment and regardless of its exact source and/or format, path data 360 received by system 300 may be stored in data store 350 for further processing.

Path data 360 received by system 300 from any or all of these sources can comprise data related to a path or plurality of paths to be analyzed by system 300. Path data 360 for a path may comprise information identifying a sequence of points included in the path, and possibly other path related information. For example, for a scanpath, path data 360 may comprise information related to a sequence of fixation points defining the scanpath. Path data 360 may optionally include other information related to a scanpath such as the duration of each fixation point, inter-fixation angles, inter-fixation distances, etc. Additional details of exemplary scanpaths as they relate to an exemplary stimulus image are described below with reference to FIG. 4.

Path data analyzer 340 can be configured to process path data 360 and, for example, identify patterns within the path data. For example, path data analyzer 340 can receive a set of path data 360 representing multiple scanpaths and can analyze these scanpaths to identify patterns, i.e., similar or matching portions therein. According to one embodiment, the path data analyzer can include a dotplot generator 380 and dotplot analyzer 390. Dotplot generator 380 can be adapted to generate a dotplot such as illustrated in and describe below with reference to FIG. 5. Such a dotplot can accept as input, or be generated based on sequences related to each scanpath of the path data. Dotplot analyzer 390 can then, based on the dotplot, identify patterns within the scanpaths. For example, dotplot analyzer 390 can perform a linear regression process on the dots in the dotplot as described below with reference to FIG. 9 to identify sequential matches between the paths or portions of the paths, i.e., between two or more sub-sequences of fixation points. In some cases, sequential matches between two or more scanpaths can be used to generate a new scanpath, which can be thought of as an "aggregate" or representative scanpath in that it represents matching tokens in both scanpaths that occur in the same sequential order.

Path analysis system 300 can also include renderer 330. Renderer 330 can be configured to receive the dotplot generated by dotplot generator 380 and/or an output of dotplot analyzer 390 and provide, e.g., via user interface 320, a display or other representation of the results. For example, renderer 330 may provide a graphical representation of the dotplot including an indication, e.g., highlighting, shading, coloring, etc. indicating portions containing matches or identified patterns. Additionally or alternatively, renderer 330 may provide a graphical representation of the scene or stimulus image for which the eye tracking data was obtained with a representation of the aggregated scanpaths presented thereon as illustrated in and described in greater detail below with reference to FIG. 6.

As noted above, the path data 360, i.e., information regarding the fixation points and saccadic eye movements between the fixation points, may be gathered using eye tracking devices such as devices capable of capturing information related to the saccadic eye activity including location of fixation points, fixation durations, and other data related to a scene or stimulus image while the user views the scene or image. Such a stimulus image can comprise, for example, a webpage or other user interface which, based on analysis of various scanpaths may be evaluated for possible improvements to the format or layout thereof.

Figure 4:
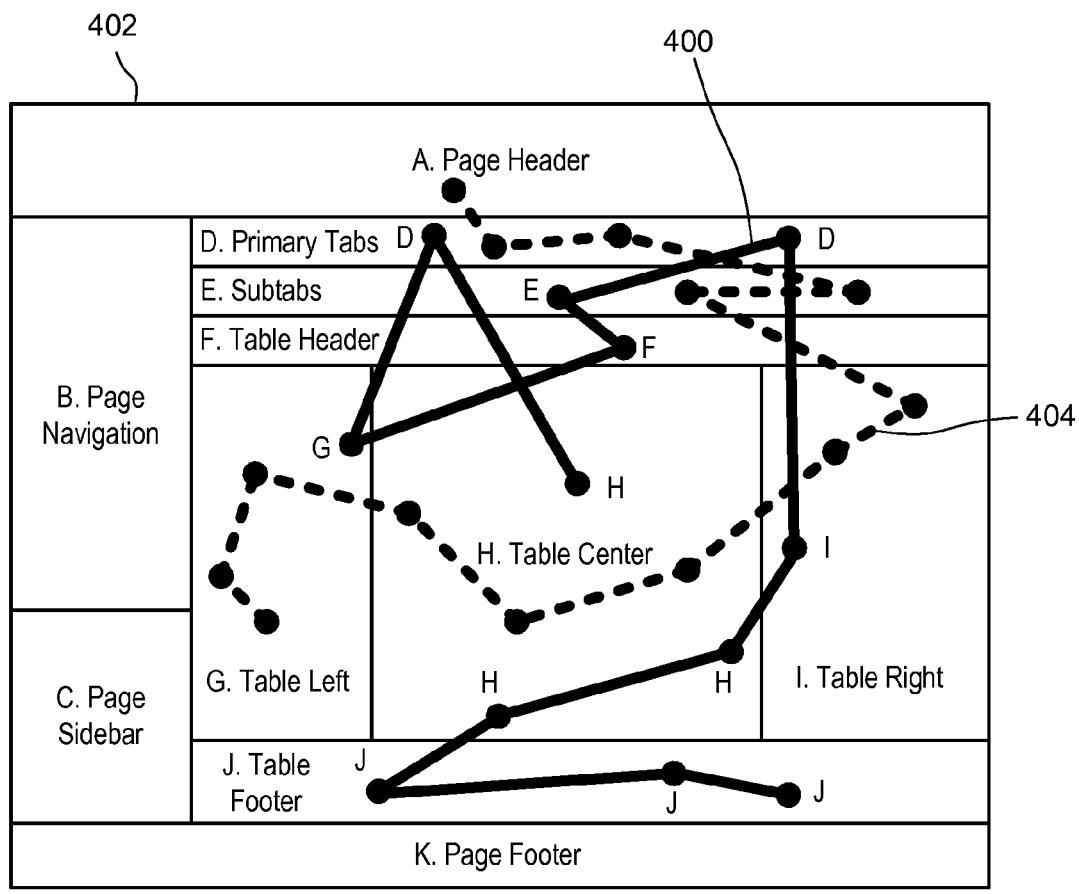
FIG. 4 illustrates an exemplary stimulus image of a user interface which may be used with embodiments of the present invention and a number of exemplary scanpaths.

FIG. 4 illustrates an exemplary stimulus image of a user interface which may be used with embodiments of the present invention and a number of exemplary scanpaths. It should be noted that this stimulus image and user interface are provided for illustrative purposes only and are not intended to limit the scope of the present invention. Rather, any number of a variety of different stimulus images, user interfaces, or means and/or methods of obtaining a query sequence are contemplated and considered to be within the scope of the present invention.

In this example, the image, which can comprise for example a web page 402 or other user interface of a software application, includes a number of elements which each, or some of which, can be considered a particular region of interest. For example, webpage 402 may be considered to comprise multiple regions such as: A (page header), B (page navigation area), C (page sidebar), D (primary tabs area), E (subtabs area), F (table header), G (table left), H (table center), I (table right), J (table footer), and K (page footer). Webpage 402 may be displayed on an output device such as a monitor and viewed by the user.

FIG. 4 also depicts exemplary scanpaths 400 and 404 representing eye movements of one or more users while viewing the webpage 402 and obtained or captured by an eye tracking device as described above. Paths 400 and 404 shows the movements of the users' eyes across the various regions of page 402. The circles depicted in FIG. 4 represent fixation points. A fixation point marks a location in the scene where the saccadic eye movement stops for a brief period of time while viewing the scene. In some cases, a fixation point can be represented by, for example, a label or name identifying a region of interest of the page in which the fixation occurs. So for example, scanpath 400 depicted in FIG. 4 may be represented by the following sequence of region names {H, D, G, F, E, D, I, H, H, J, J, J}.

The scanpath data gathered by an eye tracker can be used by embodiments of the present invention to identify patterns within the path data. For example, a set of path data representing multiple scanpaths and can be analyzed to identify patterns, i.e., similar or matching portions therein. According to one embodiment, a dotplot can be generated that includes matches between region names in each scanpath of the path data. The dotplot can then be analyzed to identify patterns within the scanpaths.

Figure 5:
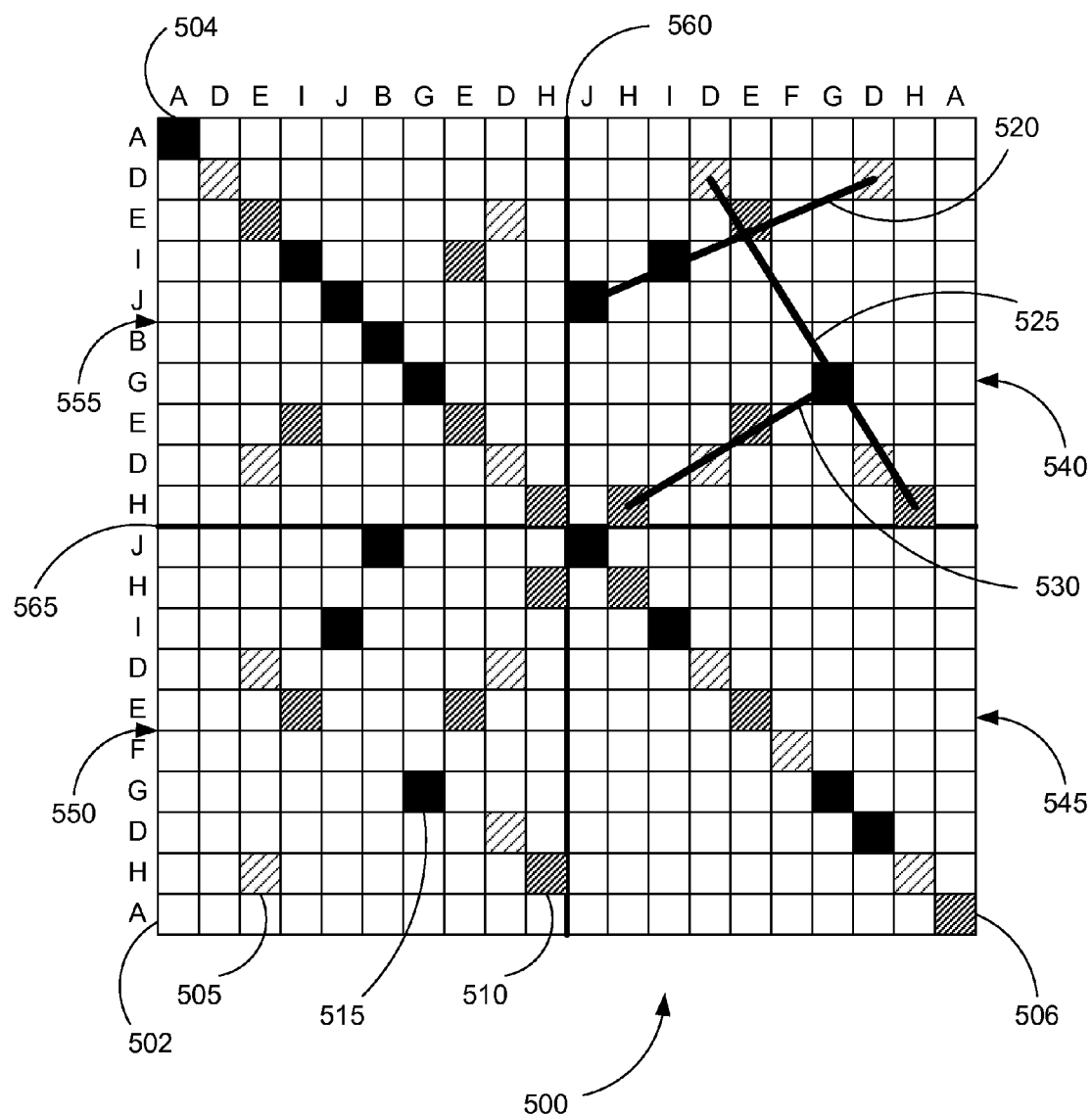
FIG. 5 is chart illustrating an exemplary dotplot for sequences of data according to one embodiment of the present invention.

FIG. 5 is a chart illustrating an exemplary dotplot for sequences of data according to one embodiment of the present invention. Generally speaking, a dotplot 500 such as illustrated in this example is a graphical technique for visualizing similarities within a sequence of tokens or between two or more concatenated sequences of tokens. For example, in one embodiment sequences of tokens may be formed from scanpath data by substituting the name of a pre-defined region of interest on a stimulus image for each scanpath fixation on that image. Dotplot 500 can be created by listing one string or sequence, represented by and corresponding to the sequence of region of interest names, on the horizontal axis 504 and on the vertical axis 502 of a matrix. Such a matrix is symmetric about a main upper-left to lower-right diagonal 506. Dots, e.g., 505, 510, and 515, can be placed in an intersecting cell of matching tokens. Additionally, these dots e.g., 505, 510, and 515, can be weighted to emphasize tokens that are more likely to be meaningful for particular applications. For example, and according to one embodiment, tokens can be inverse-frequency weighted to down-weight regions that are fixated extremely often or are otherwise trivial or uninteresting, making it easier to discover more significant eye movement patterns. This weighting can be shown on the dotplot 500 in color or shading and is illustrated in this example in dots with light hatching, e.g., 505, dots with heavy hatching, e.g., 510, and solid dots, e.g., 515. While three levels of weighting are illustrated here for the sake of clarity, it should be noted that embodiments of the present invention are not so limited. Similarly, it should be noted that the dotplot 500 illustrated in this example is significantly simplified for the sake of brevity and clarity but should not be considered as limiting on the type or extent of the dataset that can be handled by embodiments of the present invention. Rather, it should be understood that datasets for various implementations and embodiments and the corresponding dotplots can be extensive. Weighting can be applied based on different considerations. For example, when a large dataset, i.e., a large number of scanpaths, is analyzed resulting in a very large or complex dotplot, various tokens, i.e., fixation points, can be weighted based on their relative importance or interest.

As noted above, each token of the sequence of tokens represented in the dotplot 500 can correspond to a sequence of visual fixations within a set of regions of interest on a stimulus image. In such cases and as illustrated here, each token can comprise a region name identifying one of a plurality of regions of interest of the stimulus image in which the corresponding visual fixation is located. However, it should be understood that, in other embodiments, other identifiers can be used. For example, fixation duration, time between fixations, distance between fixations (a.k.a. saccade length), angles between fixations, etc. It should be understood that, while tokens comprising or representing region names may be useful when graphing or displaying results as will be described below with reference to FIG. 6, these other types of tokens can be equally useful, even if not used for graphing or displaying results, and are also considered to be within the scope of the present invention.

The dotplot 500 can be used to identify matches and reverse matches between sequences of data points or tokens. Such sequences are represented in the dotplot 500 in this example by lines 520, 525, and 530 through the dots of the particular sequence. For example, line 520 represents the sequence of tokens "JIED." Similarly, line 525 represents the sequence "DEGDH" and line 530 represents the sequence "HDEG." According to one embodiment, these sequences can be identified based on line fitting processes such as various linear regression processes including but not limited to a process such as described below with reference to FIG. 9.

Stated another way, strings comprising tokens corresponding to the region of interest in which a fixation point is detected can be concatenated and cross-plotted in a dotplot 500, placing a dot in matching rows and columns as illustrated in FIG. 5. The dotplot 500 can contain both self-matching scanpath sub-matrices along the diagonal and cross-matching scanpath sub-matrices off the main diagonal. For example and as illustrated here, the dotplot can include sub-matrices 540, 545, 550, and 555 in four quadrants of the dotplot 500 and separated here for illustrative purposes by bold vertical and horizontal lines 560 and 565. It should be understood that this example has a single distinct sub-matrix 540 because its input consists of just two sequences. In general, if a dotplot's input consists of N sequences, there will be N*(N−1)/2 distinct sub-matrices. Each cross-matching sub-matrix contains dots or points that correspond to the tokens that match between two scanpaths. Note that although each cross-matching sub-matrix appears twice, both in the upper right and again, transposed, in the lower left, each cross-matching sub-matrix need be examined only once to find matches between all pairs of scanpaths as described below and in FIG. 9.

Matching sequences between the strings can be found, for example, by fitting linear regression lines through filled cells. For example, the isolated sub-matrix 540 illustrated in FIG. 5 shows that three patterns were located: (1) line 525 "DEGDH", a matching pattern relationship from fixating the regions of interest (D) Primary Tabs, (E) Subtabs, (G) Table Left, (D) Primary Tabs, then (H) Table Center of the stimulus image of FIG. 4; (2) line 530 "HDEG", a reverse match from moving between the regions of interest (H) Table Center, (D) Primary Tabs, (E) Subtabs, and (G) Table Left; and (3) line 520 "JIED", a second reverse match moving vertically along the right side of the page, i.e., (J) Table Footer (I) Table Right (E) Subtabs and (D) Primary Tabs of the stimulus image of FIG. 4.

It should be understood that such a dotplot 500 can be used to represent any variety of different types of data. For example, the data can represent protein, DNA, and RNA sequences and the dotplot 500 can be used to identify insertions, deletions, matches, and reverse matches in the data. In another example, the data can represent text sequences and the dotplot can be used to identify the matching sequences in literature, detect plagiarism, align translated documents, identify copied computer source code, etc. According to one embodiment, the dataset can represent eye tracking data, i.e., data obtained from a system for tracking the movements of a human eye. In such cases, tokens can represent fixation points, e.g., on particular regions of interest on a user interface, and the sequences can represent scanpaths or movements of the eye between the regions.

Regardless of exactly what type dataset is used, embodiments described herein can include identifying patterns of sequential matches within the scanpaths or portions of the paths. In some cases, two scanpaths can be aggregated, i.e., an aggregated scanpath can be generated, based on and representing the identified patterns. As noted above, once patterns have been identified within the scanpaths and two scanpaths are aggregated to represent the identified pattern(s), a representation of the results can be provided. For example, a graphical representation of the dotplot 500 can be provided including an indication, e.g., highlighting, shading, coloring, etc. of portions containing matches or identified patterns. Additionally or alternatively, a graphical representation of the scene or stimulus image for which the eye tracking data was obtained can be provided. In such a case, the representation of the stimulus image can include a representation or indication of the aggregated scanpath(s), for example, displayed with or overlaid on the stimulus image.

Figure 6:
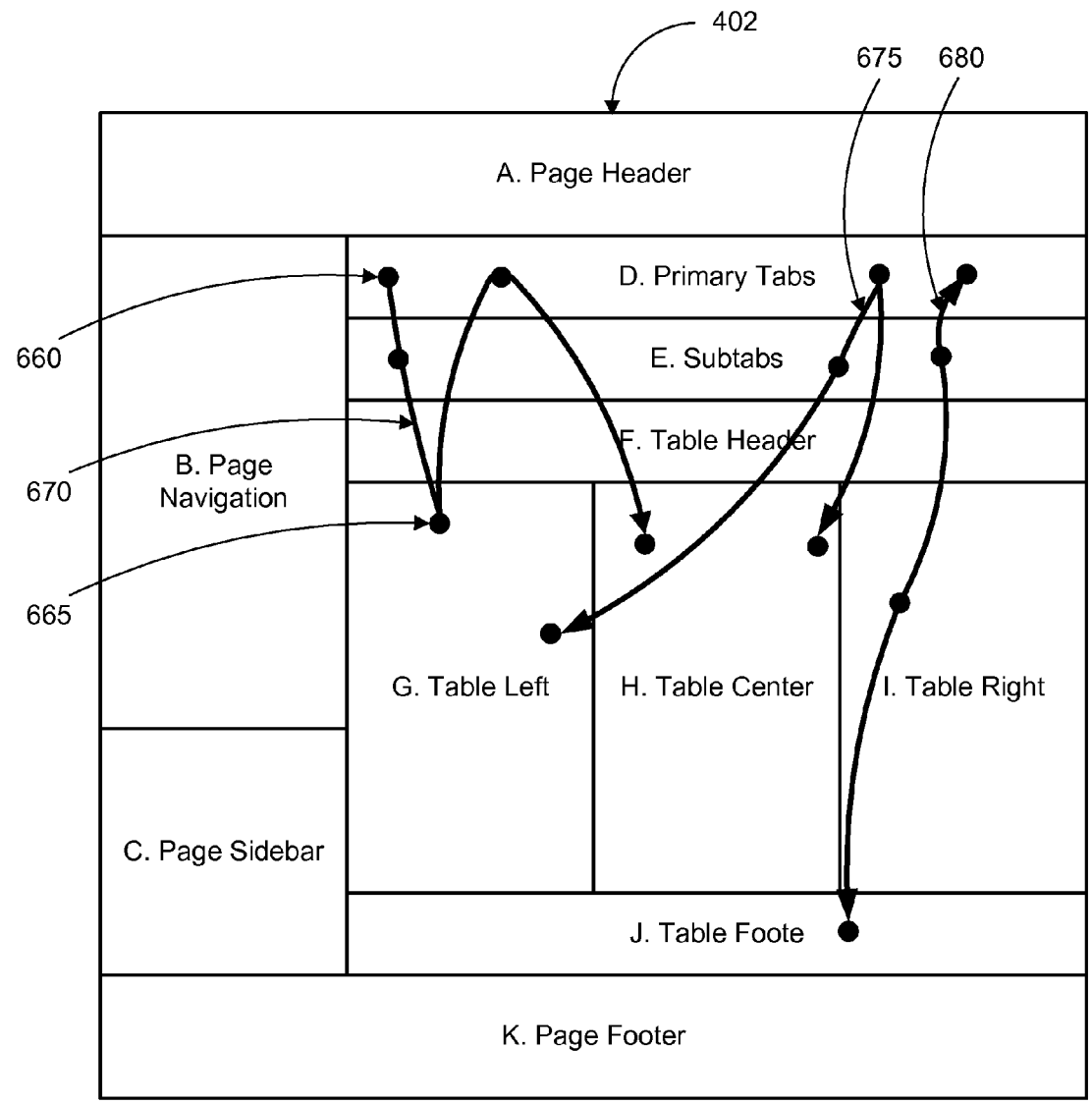
FIG. 6 illustrates an exemplary stimulus image with aggregated scanpaths displayed thereon according to one embodiment of the present invention.

FIG. 6 illustrates an exemplary stimulus image with matching scanpaths displayed thereon according to one embodiment of the present invention. In this example, the image comprises the web page 402 described above with reference to FIG. 4. That is, the stimulus image can be displayed and the patterns identified can be indicated thereon. These patterns can be presented or visualized on the stimulus image as a set of nodes, e.g., 660 and 665 and arcs connecting defined regions of the stimulus image.

So for example, FIG. 6 includes line 670 corresponding to line 525 of FIG. 5, i.e., a matching pattern relationship from fixations within the regions of interest (D) Primary Tabs, (E) Subtabs, (G) Table Left, (D) Primary Tabs, then (H) Table Center of the stimulus image. Similarly, line 675 of FIG. 6 corresponds to line 530 of FIG. 5, i.e., the reverse match from moving between the regions of interest (H) Table Center, (D) Primary Tabs, (E) Subtabs, and (G) Table Left. Also, line 680 of FIG. 6 corresponds to line 520 of FIG. 5, i.e., a second reverse match moving vertically along the right side of the page, i.e., (J) Table Footer (I) Table Right (E) Subtabs and (D) Primary Tabs.

Figure 7:
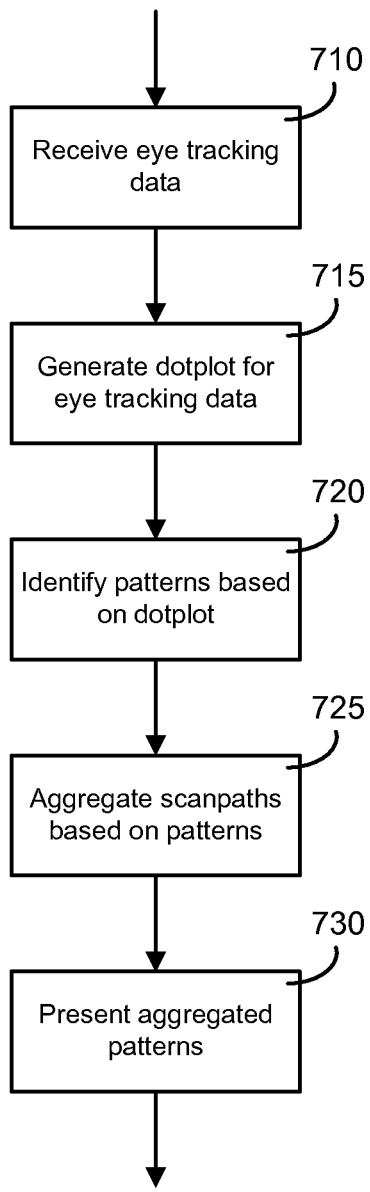
FIG. 7 is a flowchart illustrating a process for analyzing eye tracking data according to one embodiment of the present invention.

FIG. 7 is a flowchart illustrating a process for analyzing eye tracking data according to one embodiment of the present invention. In this example, the process can begin with receiving 710 the eye tracking data. As described above, the eye tracking data can comprise a plurality of scanpaths, each of the plurality of scanpaths representing a sequence of fixations in various regions of interest on a stimulus image. A dotplot representing matches between each of the scanpaths can be generated 715. Generating 715 the dotplot can comprise generating a sequence of tokens corresponding to the sequence of visual fixations. For example, each token of the sequence of tokens corresponding to the sequence of visual fixations can comprise a region name identifying one of a plurality of regions of interest of the stimulus image in which the corresponding visual fixation is located. The dotplot can then be generated using the sequence of tokens.

One or more patterns can be identified 720 within the eye tracking data based on the dotplot. According to one embodiment, identifying 720 one or more patterns can comprise identifying linear relationships within the plurality of scanpaths. For example, identifying linear relationships within the plurality of scanpaths can be based on a linear regression process such as described below with reference to FIG. 9.

Two scanpaths of the plurality of scanpaths can be aggregated 725 based on the identified one or more patterns. In some cases, a representation of the aggregated two or more scanpaths can be presented 730. For example, in the case of path data associated with spatial positions, such as eye-tracking data, the representation of the aggregated scanpaths can comprise a graphical representation of the stimulus image such as illustrated in and described above with reference to FIG. 6. As described above, the representation can also include an indication of the aggregated two or more scanpaths wherein nodes or points on the image represent fixations within a region of interest. Lines connecting the nodes can represent the aggregated scanpath.

As noted above, while embodiments of the present invention have been described in context of scanpaths, this is not intended to limit the scope of the present invention as recited in the claims to scanpaths. Teachings of the present invention may also be applied to other types of paths or sequential data occurring in various different domains. Generally speaking, sequential data can comprise a plurality of sequences and each of the plurality of sequences can represent an ordered sequence of tokens of different possible types. For example, the tokens may represent data points comprising Uniform Resource Locators (URLs) and the sequences can represent sequences of requested URLs in a client web browsing session. Similarly but in a different context, the tokens can represent data points comprising URLs and the sequences can represent sequences of requested URLs in a web server log file. In such cases, identifying patterns in such sequential data may be part of a process of evaluating the habits or workflows of one or more users. In another example, the tokens may represent data points comprising text strings and the sequences can represent sequences of the strings within one or more documents. In such cases, identifying patterns in such sequential data may, for example, be part of a process of detecting plagiarism or copying. In other cases, the tokens can represent data points comprising stock prices and the sequences can represent the stock prices over time. In still another example, the tokens may represent genes and the sequences can represent sequences of DeoxyriboNucleic Acid (DNA) or RiboNucleic Acid (RNA). Other types of sequential data are contemplated and considered to be within the scope of the present invention. Regardless of the exact source of the sequential data or what the data points represent, such sequences can be analyzed to identify patterns, i.e., matches or partial matches, therein.

Figure 8:
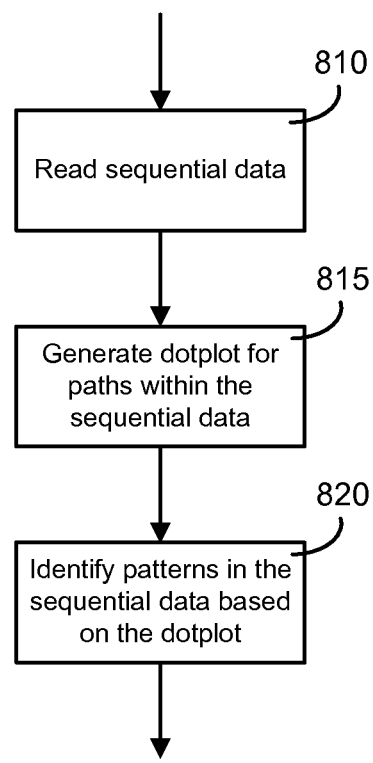
FIG. 8 is a flowchart illustrating a process for identifying patterns within sequences of data points according to one embodiment of the present invention.

FIG. 8 is a flowchart illustrating a process for identifying patterns within sequences of data points according to one embodiment of the present invention. In this example, the process begins with reading 810 a set of sequential data, for example, from memory, through a user interface, from another device or system, etc. The sequential data can comprises a plurality of sequences and each of the plurality of sequences can represent an ordered sequence of tokens of different possible types as noted above. A dotplot representing matches between each sequence of the plurality of sequences can be generated 815 based on the tokens and one or more patterns within the sequential data can be identified 820 based on the dotplot. As described above, identifying 820 one or more patterns can additionally or alternatively comprise identifying linear relationships, either direct or inverse, within the plurality of paths, for example based on a linear regression.

While not illustrated here for the sake of simplicity, it should be understood that, once identified, patterns within the sequential data can be further processed or provided to a user. For example, matching sequences can be aggregated and the aggregated sequence can be displayed on a user interface, e.g., on a chart illustrated the sequential data. In other cases, matching sequences can indicated through a user interface by highlighting text, creating and displaying hyperlinks between sequences, highlighting, shading, or coloring portions of a displayed dotplot, etc.

Regardless of the type of hardware and/or software used, embodiments of the present invention provide for analyzing sequential data representing sequences such as eye tracking data. The eye tracking data or other sequential data comprising an ordered set of tokens representing sequences can be analyzed, for example, to find sequential patterns or commonality between the scanpaths. Generally speaking, a dotplot can be generated as described above based on the tokens and can represent matches between each sequence of the plurality sequences. One or more patterns within the sequential data can then be identified based on the dotplot. For example, linear relationships in the dotplot can be detected using least-squares regression. Weighted or un-weighted regression may be conducted directly on the weighted data mentioned above. An exemplary algorithm for identifying patterns in the dotplot can be outlined as follows:

1. Start with an inverse-frequency weighted dotplot sub-matrix comparing two string sequences. Dots in the sub-matrix correspond to matching tokens in the corresponding sub-sequences. A high-pass threshold can be applied to the dots to determine an initial set of points to use for the regression, e.g., a threshold of 0.1-0.5, using a criterion of $1\mu+1\sigma$.
2. Fit a linear regression to the points. If $R^2$ value is too low (e.g., under 0.5), there is no evidence for a line. Return to Step 1, and continue to the next dotplot sub-matrix.
3. Determine the distribution of distances of the points to the line, e.g. compute $1\mu+1\sigma$ criterion from Euclidean distances between the regression line and the data points.
4. Re-compute the regression, using data that are close to the regression line (e.g., within $1\mu+1\sigma$).
5. Identified points represent sequential matches (negative slopes) or reverse sequential matches (positive slopes). Output the sequential matches, and remove the identified points from the original set of filtered points. Return to Step 2, to possibly locate another linear relationship in the remaining points.

Figure 9:
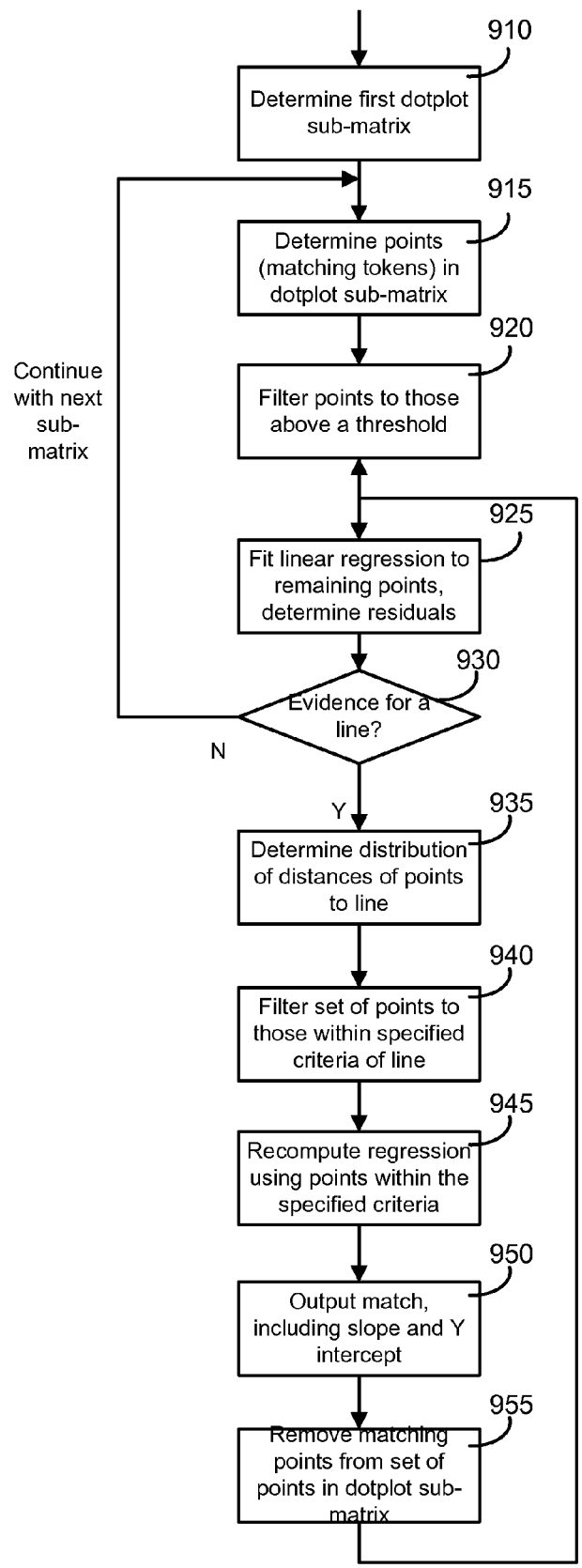
FIG. 9 is a flowchart illustrating a linear regression process for identifying patterns within a dotplot of sequential data according to one embodiment of the present invention.

FIG. 9 is a flowchart illustrating a linear regression process for identifying patterns within a dotplot of sequential data according to one embodiment of the present invention. In this example, processing begins with determining 910 a dotplot sub-matrix comparing the tokens of two scanpaths. Points in the sub-matrix correspond 915 to matching tokens in the corresponding sub-sequences. A high-pass threshold can be applied 920 to the dots to determine an initial set of points to use for the regression (e.g., a threshold of 0.1-0.5, using a criterion of 1μ+1σ) and a linear regression line can be fitted 925 to the filtered points. A determination can be made 930 as to whether there is sufficient statistical evidence for a line. For example, if 930 the $R^2$ value is too low (e.g., under 0.5), there is no line. In response to determining 930 that no line exists, processing can continue with another dotplot sub-matrix, if any, i.e., by returning to determining points in the next sub-matrix 915.

In response to determining 930 that a line exists within the filtered points, variance criterion (1μ+1σ) can be computed 935 based on Euclidean distances between the regression line and the filtered points. The set of points can then be further filtered 940 to those within the variance criterion, i.e., within 1μ+1σ. The linear regression line can be recomputed 945 to better fit the remaining points. Information describing the new regression line (e.g. its slope, Y-intercept, and constituent points) can be output 950. Points identified as having linear relationships can be removed 955 from the set of points. In some cases, identifying one or more patterns can further comprise identifying another linear relationship within the points, if any, by repeating said fitting 925 a linear regression line to the filtered points, determining 930 whether another sequential match exists within the filtered points based on a fit of the linear regression line, computing 935 variance criterion from Euclidean distances between the regression line and the filtered points, further filtering 940 the points to those within the variance criterion, recomputing 945 the linear regression line using the filtered points within the variance criterion, outputting information about the sequential match 950, and removing 955 the points identified as having linear relationships from the set of points until no points remain in the set of points or no matches exist, i.e., the $R^2$ value is too low for the remaining points.

In the foregoing description, for the purposes of illustration, methods were described in a particular order. It should be appreciated that in alternate embodiments, the methods may be performed in a different order than that described. It should also be appreciated that the methods described above may be performed by hardware components or may be embodied in sequences of machine-executable instructions, which may be used to cause a machine, such as a general-purpose or special-purpose processor or logic circuits programmed with the instructions to perform the methods. These machine-executable instructions may be stored on one or more machine readable mediums, such as CD-ROMs or other type of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

While illustrative and presently preferred embodiments of the invention have been described in detail herein, it is to be understood that the inventive concepts may be otherwise variously embodied and employed, and that the appended claims are intended to be construed to include such variations, except as limited by the prior art.

What is claimed is:

1. A method for identifying one or more patterns in a plurality of sequences, the method comprising:
   reading a set of sequential data with an analysis system, wherein the sequential data comprises a plurality of sequences, each of the plurality of sequences representing an ordered sequence of tokens;
   generating, with the analysis system, a dotplot based on the tokens and representing matches between each sequence of the plurality sequences; and
   identifying, with the analysis system, one or more patterns within the sequential data based on the dotplot by identifying linear relationships between the tokens and wherein identifying linear relationships between the tokens comprises:
      determining a dotplot sub-matrix plotting tokens from two sequences;
      identifying a set of points in the sub-matrix that corresponds to matching tokens in corresponding sub-sequences;
      filtering the identified points against a pre-determined high-pass threshold;
      fitting a linear regression line to the filtered points;
      computing variance criterion based on Euclidean distances between the regression line and the filtered points;
      filtering the filtered points to those within the variance criterion; and
      re-computing the linear regression line using the points within the variance criterion.

2. The method of claim 1, wherein identifying one or more patterns further comprises removing the points having linear relationships from the set of points, identifying another linear relationship within the dataset by repeating said fitting a linear regression line to the filtered points, computing variance criterion based on Euclidean distances between the regression line and the filtered points, filtering the filtered points to those within the variance criterion, and re-computing the linear regression line using the points within the variance criterion.

3. The method of claim 2, wherein the tokens represent data points comprising fixation points of eye tracking data and the sequences represent scanpaths.

4. The method of claim 2, wherein the tokens represent data points comprising Uniform Resource Locators (URLs) and the sequences represent sequences of requested URLs in a client web browsing session.

5. The method of claim 2, wherein the tokens represent data points comprising Uniform Resource Locators (URLs) and the sequences represent sequences of requested URLs in a web server log file.

6. The method of claim 2, wherein the tokens represent data points comprising text strings and the sequences represent sequences of the strings within one or more documents.

7. The method of claim 2, wherein the tokens represent data points comprising stock prices and the sequences represent the stock prices over time.

8. The method of claim 2, wherein the tokens represent genes and the sequences represent sequences of Deoxyribo-Nucleic Acid (DNA) or RiboNucleic Acid (RNA).

9. A system for identifying one or more patterns in a plurality of sequences, the system comprising:
   a processor; and
   a memory communicatively coupled with and readable by the processor and having stored therein a series of instructions which, when executed by the processor, cause the processor to read a set of sequential data, wherein the sequential data comprises a plurality of sequences, each of the plurality of sequences representing an ordered sequence of tokens, generate a dotplot representing matches between each sequence of the plurality sequences, and identify one or more patterns within the sequential data based on the dotplot by identifying linear relationships between the tokens and wherein identifying linear relationships between the tokens comprises:
- determining a dotplot sub-matrix plotting tokens from two sequences;
- identifying a set of points in the sub-matrix that corresponds to matching tokens in corresponding sub-sequences;
- filtering the identified points against a pre-determined high-pass threshold;
- fitting a linear regression line to the filtered points;
- computing variance criterion based on Euclidean distances between the regression line and the filtered points;
- filtering the filtered points to those within the variance criterion; and
- re-computing the linear regression line using the points within the variance criterion.

10. The system of claim 9, wherein identifying one or more patterns further comprises removing the points having linear relationships from the set of points, identifying another linear relationship within the dataset by repeating said fitting a linear regression line to the filtered points computing variance criterion based on Euclidean distances between the regression line and the filtered points, filtering the filtered points to those within the variance criterion, and re-computing the linear regression line using the points within the variance criterion.

11. The system of claim 9, wherein the tokens represent data points selected from a group consisting of: fixation points of eye tracking data; Uniform Resource Locators (URLs); text strings; stock prices; and genes.

12. A machine-readable memory device having stored thereon a series of instructions which, when executed by a processor, cause the processor to identify one or more patterns in a plurality of sequences by:
- reading a set of sequential data, wherein the sequential data comprises a plurality of sequences, each of the plurality of sequences representing an ordered sequence of tokens;
- generating a dotplot representing matches between each sequence of the plurality sequences; and
- identifying one or more patterns within the sequential data based on the dotplot by identifying linear relationships between the tokens and wherein identifying linear relationships between the tokens comprises:
  - determining a dotplot sub-matrix plotting tokens from two sequences;
  - identifying a set of points in the sub-matrix that corresponds to matching tokens in corresponding sub-sequences;
  - filtering the identified points against a pre-determined high-pass threshold;
  - fitting a linear regression line to the filtered points;
  - computing variance criterion based on Euclidean distances between the regression line and the filtered points;
  - filtering the filtered points to those within the variance criterion; and
  - re-computing the linear regression line using the points within the variance criterion.

13. The machine-readable memory device of claim 12, wherein identifying one or more patterns further comprises removing the points having linear relationships from the set of points, identifying another linear relationship within the dataset by repeating said fitting a linear regression line to the filtered points, computing variance criterion based on Euclidean distances between the regression line and the filtered points, filtering the filtered points to those within the variance criterion, and re-computing the linear regression line using the points within the variance criterion.

14. The machine-readable memory device of claim 12, wherein the tokens represent data points selected from a group consisting of: fixation points of eye tracking data and wherein the sequences represent scanpaths; Uniform Resource Locators (URLs) and wherein the sequences represent sequences of requested URLs in a client web browsing session or requested URLs in a web server log file; text strings and wherein the sequences represent sequences of the strings within one or more documents; stock prices and wherein the sequences represent the stock prices over time; and genes and wherein the sequences represent sequences of Deoxyribo-Nucleic Acid (DNA) or RiboNucleic Acid (RNA).

* * * * *

UNITED STATES PATENT AND TRADEMARK OFFICE
CERTIFICATE OF CORRECTION

PATENT NO. : 8,463,733 B2  
APPLICATION NO. : 12/615749  
DATED : June 11, 2013  
INVENTOR(S) : Helfman et al.

Page 1 of 1

It is certified that error appears in the above-identified patent and that said Letters Patent is hereby corrected as shown below:

In the Claims

In column 17, line 24, in Claim 10, delete "points" and insert -- points, --, therefor.

Signed and Sealed this
Eighth Day of October, 2013

Teresa Stanek Rea
*Deputy Director of the United States Patent and Trademark Office*